United States Patent
Puniya et al.

(10) Patent No.: US 10,493,034 B2
(45) Date of Patent: Dec. 3, 2019

(54) PHARMACEUTICAL COMPOSITION FOR TREATMENT OF HIV INFECTION

(71) Applicants: OTKRYTOE AKTSIONERNOE OBSCHESTVO "FARMASYNTEZ", g. Irkutsk (RU); Vikram Singkh Puniya, Irkutskaya (RU)

(72) Inventors: Vikram Singkh Puniya, Irkutskaya (RU); Gennady Andreevich Batyunin, Irkutsk (RU); Natalya Yurievna Malykh, g. Irkutsk (RU)

(73) Assignee: OTKRYTOE AKTSIONERNOE OBSCHESTVO "FARMASYNTEZ" (RU)

( * ) Notice: Subject to any disclaimer, the term of this patent is extended or adjusted under 35 U.S.C. 154(b) by 0 days.

(21) Appl. No.: 14/753,395

(22) Filed: Jun. 29, 2015

(65) Prior Publication Data
US 2015/0297526 A1 Oct. 22, 2015

Related U.S. Application Data

(63) Continuation of application No. PCT/RU2013/000817, filed on Sep. 19, 2013.

(30) Foreign Application Priority Data

Dec. 29, 2012 (RU) .............................. 2012158141

(51) Int. Cl.
| | | |
|---|---|---|
| *A61K 9/20* | (2006.01) | |
| *A61K 31/427* | (2006.01) | |
| *A61K 31/513* | (2006.01) | |
| *A61K 31/27* | (2006.01) | |
| *A61K 31/33* | (2006.01) | |
| *A61K 31/505* | (2006.01) | |
| *A61K 31/63* | (2006.01) | |
| *A61K 9/48* | (2006.01) | |

(52) U.S. Cl.
CPC .......... *A61K 9/2054* (2013.01); *A61K 9/2013* (2013.01); *A61K 9/2018* (2013.01); *A61K 9/2027* (2013.01); *A61K 9/2077* (2013.01); *A61K 9/4858* (2013.01); *A61K 31/27* (2013.01); *A61K 31/33* (2013.01); *A61K 31/427* (2013.01); *A61K 31/505* (2013.01); *A61K 31/513* (2013.01); *A61K 31/63* (2013.01)

(58) Field of Classification Search
CPC .................................................. A61K 9/2054
USPC .......................................................... 514/274
See application file for complete search history.

(56) References Cited

U.S. PATENT DOCUMENTS

| | | | |
|---|---|---|---|
| 5,484,926 A | 1/1996 | Dressman et al. | |
| 8,691,878 B2 | 4/2014 | Rosenberg et al. | |
| 2010/0173921 A1* | 7/2010 | Lulla .................... | A61K 9/2077 514/274 |
| 2011/0034489 A1* | 2/2011 | Tiwari ................... | A61K 9/146 514/274 |

FOREIGN PATENT DOCUMENTS

| | | |
|---|---|---|
| EA | 011924 B1 | 6/2009 |
| WO | 2005039551 A2 | 5/2005 |

OTHER PUBLICATIONS

Eudragot E100 (2015) material data.*
Kollidon VA64 BASF_Mar. 2000.*
English translation of the International Search Report issued by the International Bureau dated Mar. 7, 2014 for corresponding international patent application No. PCT/RU2013/000817.
English translation of the International Preliminary Report on Patentability issued by the International Bureau dated Jun. 30, 2015 for corresponding international patent application No. PCT/RU2013/000817.
English translation of the Written Opinion issued by the International Searching Authority dated Feb. 20, 2014 for corresponding international patent application No. PCT/RU2013/000817.
Barabas, Eugene S. and Christianah M. Adeyeye. Crospovidone. Analytical Profiles of Drug Substances and Excipients, vol. 24, 1st Edition. Jul. 25, 1996. pp. 87-163.
Shin-Etsu Chemical Co., LTD. Low-Substituted Hydroxypropyl Cellulose NF. L-HPC. pp. 1-23.

* cited by examiner

*Primary Examiner* — Yong L Chu
(74) *Attorney, Agent, or Firm* — Michele L. Lawson; Smith & Hopen, P.A.

(57) ABSTRACT

The invention is a pharmaceutical composition for the treatment of HIV infection; containing at least one HIV protease inhibitor as an active ingredient, as well as pharmaceutically acceptable excipients with a specific quantitative component ratio. Additionally, the invention belongs to the process of its production and to a treatment method. The inventive pharmaceutical composition has increased bioavailability and improved technological properties, such as durability, plasticity, disintegration, compared to the prototype drug.

17 Claims, 1 Drawing Sheet

Mean lopinavir dissolution profile in drugs Kalidavir and Kaletra.
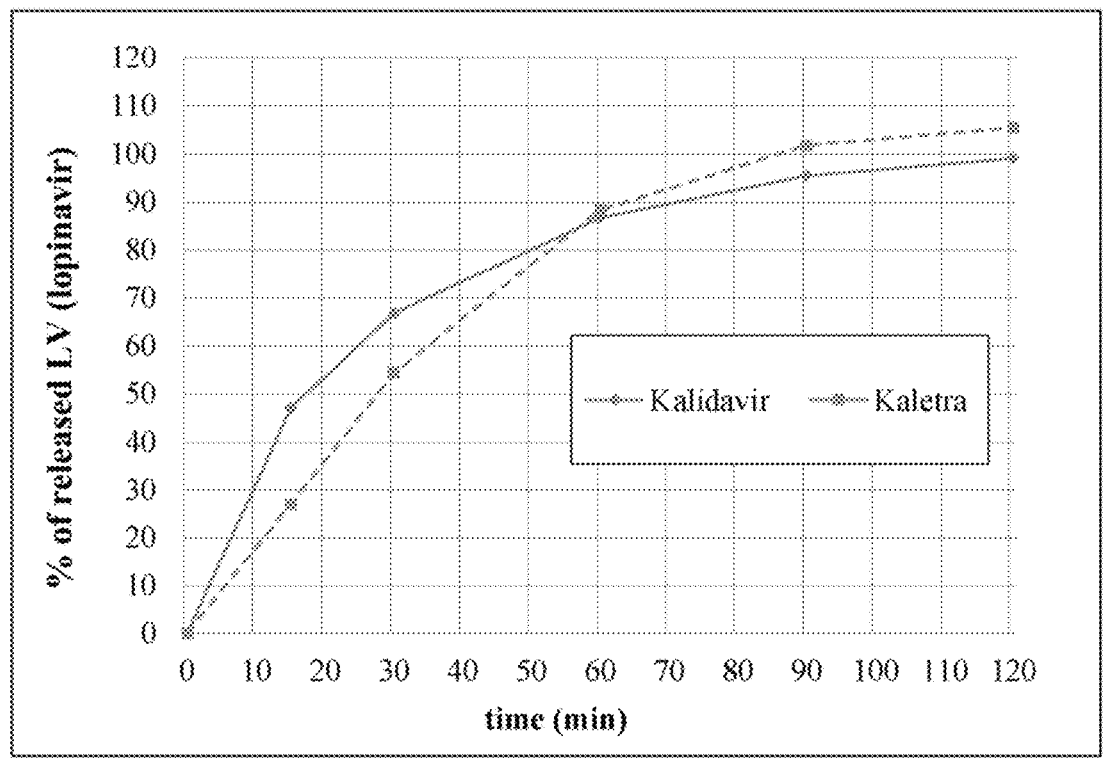
The Figure

PHARMACEUTICAL COMPOSITION FOR TREATMENT OF HIV INFECTION

CROSS-REFERENCE TO RELATED APPLICATIONS

This nonprovisional application is a continuation of and claims priority to International Patent Application No. PCT/RU2013/000817 entitled "Pharmaceutical Composition for Treatment of HIV Infections," filed Sep. 19, 2013, which claims priority to Russian Patent Application No. 2012158141, having the same title and a filing date of Dec. 29, 2012, both of which are herein incorporated by reference.

BACKGROUND OF THE INVENTION

1. Field of the Invention

The invention relates to the field of chemical and pharmaceutical industry, specifically to a pharmaceutical composition for treatment of HIV infection, which contains at least one HIV protease inhibitor as an active ingredient, as well as pharmaceutically acceptable excipients with a specific quantitative component ratio. Additionally, the invention relates to a production process and to a treatment method.

2. Brief Description of the Related Art

According to the UN data, the number of HIV-positive people is 34.2 million. There is not a single country that has not been affected by this truly global epidemic.

In the Russian Federation the epidemiologic situation for HIV infection remains difficult, the spread of the human immunodeficiency virus among the population continues, and the cumulative amount of infected and sick individuals grows.

According to the Rospotrebnadzor data (The Federal Service for Supervision of

Consumer Rights Protection and Human Well-Being), there are 617,018 persons currently living with HIV in the Russian Federation.

During ten months of 2012, there were 62,865 new cases of HIV infection, which is 12.5% more compared to last year. HIV-cases are reported in all subjects of the Russian Federation.

HIV protease inhibitors (PI) are HIV protease active centre agonists, which should split the Gag-pol polyprotein of the virus into separate functional proteins. As the result of inhibitor action, protease cannot perform its function, and new viral particles, incapable of infecting new cells, are created. PI often has adverse effects on gastrointestinal (GI) tract. With long-term administration, lipidosis of various degrees, as well as lipodystrophy are possible.

Among HIV protease inhibitors are nelfinavir, saquinavir, tipranavir, darunavir, indinavir, atazanavir, ritonavir, lopinavir, palinavir, fosamprenavir.

It is well-known that most HIV protease inhibitors are substances of low water solubility. This may lead to technical complications during preparation of finished dosage forms based on these substances. Additionally, it is very difficult to select such excipient composition that would not lead to a worsening of pharmacokinetic properties of the finished dosage form and, thus, to a decrease of its bioavailability.

On the technical level, there is Kaletra® film-coated tablets (Lopinavir 200 mg+Ritonavir 50 mg) manufactured at Abbott GmBH and Co.KG, Germany, which is described in EA011924 patent and which was selected as a the prototype by the authors of the said invention.

As described in EA011924 patent, the authors tried to increase bioavailability of the solid dosage form of lopinavir+ritonavir. This problem was solved through addition of a relatively large amount of water-soluble polymers (from approximately 50 to approximately 85% w/w) and a pharmaceutically acceptable surfactant (from approximately 2 to approximately 20% w/w relative to the finished dosage form weight).

Use of relatively large amounts of high-cost excipients increases the net cost of the drug.

Additionally, a major disadvantage of lopinavir/ritonavir is its ability to cause not only gastro-intestinal problems (diarrhea, nausea), but also an express dyslipoproteinemia—even more significant, than with other PIs. Like other PIs, lopinavir/ritonavir leads to lipodystrophy syndrome; its incidence rate is 15% after 5 years, according to the data of a long-term study. Additionally, when prescribing this drug it is important to consider multiple drug interactions. In combination with efavirenz and nevirapine, and possibly amprenavir, its dosage should be increased. According to the latest data, lopinavir/ritonavir should be prescribed to be administered once a day (800/200 mg), although in this case, it causes diarrhoeamore often.

Thus, there is a current need in new antiviral finished dosage forms, which inhibit HIV protease activity and have improved pharmacokinetic and technological properties, as well as increased bioavailability and, consequently, improved therapeutic effectiveness.

Authors of the said invention set the following technical goal: development of new and more effective (compared to the prototype) pharmaceutical forms of the drug (HIV protease inhibitor) with the following properties: 1) the dosage form must have improved technological properties (durability, plasticity, disintegration time etc.), as well as high stability; 2) dosage form must have improved dissolution kinetics and increased bioavailability (compared to the prototype).

Attainable technical result of the claimed invention meets the set goals and expands the variety of high-quality domestic drugs available for treatment of HIV infection; it has improved dissolution kinetics and increased biological availability, as compared to the prototype. Additionally, produced dosage forms have improved technological properties and high shelf-life stability. Attained technical results are not obvious and could not have been foreseen by a specialist on the basis of modern technology level.

BRIEF SUMMARY OF THE INVENTION

A pharmaceutical composition is provided which possesses particular use in the treatment of HIV-infection in solid dosage form. The composition comprising at least one HIV protease inhibitor in a therapeutic amount, selected from the group consisting of nelfinavir, saquinavir, tipranavir, darunavir, indinavir, ritonavir, lopinavir, palinavir, and fosamprenavir; as well as a plurality of pharmaceutically acceptable excipients. The pharmaceutically acceptable excipients include at least one water-soluble polymer in the amount of 0.4-49% w/w of the total dosage form, at least one water-insoluble polymer in the amount of 0.39-28% w/w of the total dosage form, a plurality of surfactants, and a plurality of fillers. The excipients comprise up to 100% w/w of the total dosage form.

In specific embodiments, the water-soluble polymer is copovidone. Alternatively, the water-soluble polymer is sodium starch glycolate. In other embodiments, the water-soluble polymer is croscarmellose sodium and/or homopolymers and copolymers of N-vinyl lactams and/or polyethylene oxide and/or polypropylene oxide and/or copolymers of ethylene oxide and propylene oxide and/or polyacrylates and/or polymethacrylates and/or polyacrylamides and/or vinyl acetate polymers and/or polyvinyl alcohol and/or carrageenans and/or cellulose esters and/or cellulose ethers and/or cellulose succinates.

In specific embodiments, the water-insoluble polymer is microcrystalline cellulose. Alternatively, the water-soluble polymer is low-substituted hydroxypropyl cellulose.

In certain embodiments, the plurality of surfactants is from 0.3-1.0% w/w. In embodiments of the invention, the surfactants include polysorbate 80 and/or macrogol 6000.

In certain embodiments, the filler is from 0.3-56% w/w. In some embodiments, the filler is lactose and/or modified lactose and/or sucrose and/or glucose and/or mannitol and/or modified mannitol and/or sorbitol and/or fructose and/or cellulose and/or cellulose derivatives and/or starch and/or modified starch and/or dextrin and/or dextrose and/or dextrate and/or maltodextrine and/or calcium and its salts (phosphates, carbonates, chlorides) and/or magnesium and its derivatives (oxide, carbonate, stearate), and/or crospovidone and/or copovidones and/or cyclodextrines and/or alginic acid and its salts and/or saccharine and/or its salts, and/or sodium and its salts (chloride, citrate, fumarate, carbonate) and/or aspartame and/or lactic acid and its salts and/or succinic acid and/or ascorbic acid and/or tartaric acid and/or colloidal silicon dioxide and/or cyclamate and/or benzoic acid and/or benzoic acid salts and/or parabens and/or parabens salts.

Also disclosed is a pharmaceutical composition for treating HIV infection, comprising at least one HIV protease inhibitor in therapeutic amount and pharmaceutically acceptable excipients. The HIV protease inhibitor is nelfinavir, saquinavir, tipranavir, darunavir, indinavir, atazanavir, ritonavir, lopinavir, palinavir, or fosamprenavir. The pharmaceutically acceptable excipients include pharmaceutically acceptable water-insoluble polymer in the amount from 0.39 to 28% w/w of the total finished dosage form, a plurality of surfactants; and a plurality of fillers, where the excipients comprise up to 100% of the total finished dosage form. Examples of the water-insoluble polymer include microcrystalline cellulose and/or hydroxypropyl cellulose.

The surfactants are optionally provided at 0.3-1.0% w/w of the composition.

Examples of optional surfactants include polysorbate 80 and/or macrogol 6000. The fillers are optionally provided at 0.3-56% w/w of the composition. Examples of optional fillers include lactose and/or modified lactose and/or sucrose and/or glucose and/or mannitol and/or modified mannitol and/or sorbitol and/or fructose and/or cellulose and/or cellulose derivatives and/or starch and/or modified starch and/or dextrin and/or dextrose and/or dextrate and/or maltodextrine and/or calcium and its salts (phosphates, carbonates, chlorides) and/or magnesium and its derivatives (oxide, carbonate, stearate), and/or crospovidone and/or copovidones and/or cyclodextrines and/or alginic acid and its salts and/or saccharine and/or its salts, and/or sodium and its salts (chloride, citrate, fumarate, carbonate) and/or aspartame and/or lactic acid and its salts and/or ascorbic acid and/or tartaric acid and/or colloidal silicon dioxide and/or cyclamate and/or benzoic acid and/or benzoic acid salts and/or parabens and/or parabens salts as fillers.

Also disclosed are methods of treating HIV infection by administering a therapeutically effective amount of the pharmaceutical composition described above.

BRIEF DESCRIPTION OF THE DRAWINGS

For a fuller understanding of the invention, reference should be made to the following detailed description, taken in connection with the accompanying drawings, in which:

The FIGURE is a graph showing the mean lopinavir dissolution profile in drugs Kalidavir and Kaletra.

DETAILED DESCRIPTION OF THE PREFERRED EMBODIMENT

The set goal is achieved by the fact that the inventors of the said invention developed pharmaceutical composition variations for the treatment of HIV infection that include at least one HIV protease inhibitor and pharmaceutically acceptable excipients with a specific quantitative component ratio.

Based on experimental trials, the authors of the said invention were able to significantly lower the content of water-soluble polymer in the pharmaceutical composition. Upon that it was unexpectedly discovered that dissolution kinetics and biological availability of the claimed pharmaceutical composition has improved significantly as compared to the prototype drug. Thus, the pharmaceutical composition of the described invention decreases the time until therapeutic effect is achieved and is produced through careful selection of qualitative composition and quantitative ratio of excipients.

The authors of the said invention have currently not been able to fully understand the reason behind the improvement of pharmacokinetic properties and the increase of bioavailability following the decrease of water-soluble polymers content in the finished dosage from.

The authors do not exclude the possible effect that water-soluble polymers and surfactants and their interactions have on the described improvements.

Upon creating several variations of the claimed pharmaceutical composition, it was discovered that the reported technical result is achieved, if in one of these variations (further, variation 1 of the pharmaceutical composition) the claimed pharmaceutical composition contains from 0.4 to 49% w/w (in terms of 100% w/w of the total solid dosage form) of water-soluble polymers, and if it also contains from 0.39 to 28% w/w of at least one water-insoluble polymer (of the total finished dosage form). Based on the conducted experimental trials it was discovered that with another content of water-soluble and insoluble polymers the produced finished dosage form has different (decreased as compared to the prototype) properties.

Additionally, the authors have discovered, that the technical result of the claimed invention is also achieved, if the composition in another variation (further, variation 2 of the pharmaceutical composition) of the said invention contains at least one pharmaceutically acceptable water-insoluble polymers in the amount from 0.39 to 28% w/w of the total finished dosage form, surfactants, fillers to 100% of the total finished dosage form, given that water-soluble polymers are not present.

As a result of experimental development of possible finished dosage forms it was discovered that the active substances, which can comprise the claimed pharmaceutical composition, may include nelfinavir, saquinavir, tipranavir, darunavir, indinavir, ritonavir, lopinavir, palinavir, fosamprenavir or their combinations with one another, are also known in the field and are used to treat HIV infection.

In accordance with the invention, the provided drug contains between 5.0% w/w and 60.5% of the active substance (of the total dosage form), as well as pharmaceutically acceptable excipients in the amount from 39.5% to 95.0% of the active substance weight.

Effective amount of the active HIV protease inhibitor substance in dosage form is between 5 mg and 1500 mg.

The claimed antiviral pharmaceutical composition should also preferably contain at least one additional antiviral substance (HIV protease inhibitor) for achievement of synergetic action. HIV protease inhibitors, which could comprise the pharmaceutical composition according to the said invention, may include nelfinavir, saquinavir, tipranavir, darunavir, indinavir, ritonavir, lopinavir, palinavir, or fosamprenavir.

Together with the active substance, the pharmaceutical composition may also contain regular excipients that are acceptable in the process of drug manufacturing, such as binders, fillers, preservatives, flow control agents, softeners, wetting agents, dispersing agents, emulsifiers, solvent, antioxidants and/or propellants, drug carriers. Sucker et al.: Pharmazeutische Technologie, Thieme-Verlag, Stuttgard, 1991.

Pharmaceutical compositions may contain one or more of the following substances as fillers: sugars and their derivatives (lactose, modified lactose, sucrose, glucose, mannitol, modified mannitol, fructose), polysaccharides (cellulose and its derivatives, starch, modified starch), dextrin, dextrose, dextrate, maltodextrin, calcium and its salts, (phosphates, carbonates, chlorides), magnesium and its derivatives (oxide, carbonate, stearate), crospovidone, copovidone, cyclodextrines, alginic acid and its salts, saccharine and its salts, sodium and its salts (chloride, citrate, fumarate, carbonate), aspartame, lactic acid and its salts, succinic acid, ascorbic acid, tartaric acid, colloidal silicon dioxide, cyclamate, benzoic acid and its salts, parabens and their salts.

Pharmaceutical composition should preferably contain from 0.3 to 56% w/w of the fillers mentioned above (in terms of 100% w/w of the total solid dosage form).

Water-soluble polymers that are acceptable for use in the pharmaceutical composition of the said invention may include, but are not limited to the following substances: homopolymers and copolymers of N-vinyl lactarns, especially homopolymers and copolymers of N-vinylpyrrolidone, e.g. polyvinylpyyrrolidone (PVP) copolymers of N-vinylpyrrolidone and vinyl acetate or vinyl propionate; high molecular weight polyalkylene oxides, such as polyethylene oxide and polypropylene oxide and copolymers of ethylene oxide and propylene oxide; polyacrylates and polymethacrylates, such as methacrylic acid/ethyl acrylate copolymers, methacrylic acid/methyl methacrylate copolymers, butyl methacrylate/2-(dimethylamino)ethylmethacrylate copolymers, poly(hydroxyalkylacrylates), poly(hydroxyalkylmethacrylates); polyacrylamides; vinyl acetate polymers, such as copolymers of vinyl acetate and crotonic acid; polyvinyl alcohol; oligo- and polysaccharides, such as carrageenans; cellulose esters and cellulose ethers, in particular methylcellulose and ethyl cellulose, hydroxyalkyl cellulose, in particular hydroxypropylcellulose, cellulose succinates, in particular hydroxypropylcellulose succinate or hydroxypropylcellulose acetate succinate.

Water-insoluble polymers that may be used in the said invention may include, but are not limited to the following substances: microcrystalline cellulose, low-substituted hydroxypropyl cellulose, cellulose ethers (alkyl cellulose ethers, such as ethyl cellulose, ethyl methylcellulose, ethyl propyl cellulose, isopropyl cellulose, butyl cellulose etc.; aralkyl ethers of cellulose, such as benzyl cellulose etc.; cyanoalkyl ethers of cellulose, such as cyanoethyl cellulose, etc.), cellulose esters (cellulose ethers and organic acids, such as cellulose acetate butyrate, cellulose acetate, cellulose propionate, cellulose butyrate, cellulose acetate propionate, etc.), copolymers of methacrylic acid and acrylic acid, etc.

The pharmaceutical composition should preferably contain from 0.4 to 49% w/w of the water-soluble polymers mentioned above, at least one water-insoluble polymer in the amount from 0.39 to 28% w/w of the total finished dosage form, surfactants, fillers up to 100% w/w of the total finished dosage form.

In one of the variations of the said invention, the pharmaceutical composition contains between 0.4 and 20% w/w of the water-soluble polymers mentioned above (in terms of 100% w/w of the total solid dosage form).

Surfactants that are acceptable for use in the pharmaceutical composition of the said invention may include, but are not limited to the following substances: polysorbate 80 (i.e., TWEEN-80 polysorbate), macrogol 6000 (polyethyleneglycol 6000).

The pharmaceutical composition should preferably contain between 0.3 and 1.0% w/w of surfactants (in terms of 100% w/w of the total solid dosage form).

In one of the variations of the said invention, the pharmaceutical composition contains between 0.3 and 0.9% w/w of surfactants (in terms of 100% w/w of the total solid dosage form).

In one of the variations of the said invention, the pharmaceutical composition preferably contains at least one pharmaceutically acceptable water-insoluble polymer in the amount from 0.39 to 28% w/w of the total finished dosage form, surfactants, fillers up to 100% w/w of the total finished dosage form.

The preferred ratio of water-insoluble polymers to surfactants in the claimed pharmaceutical composition should be between 39 and 93.3.

Preferably, the drug may be formulated as powders, tablets, combined tablets, capsules, dragée, film-coated granules, suppositories, powders for suspensions. Dosage forms may be formulated in the traditional way (<<Pharmacevticheskaya technologiya. Technologiya lekarstvennyh form>>, $2^{nd}$ edition, Moscow, 2006).

The pharmaceutical composition of the invention may be administered orally. Dosage depends on patient's age, health condition, and weight.

The recommended dosage of the combined lopinavir/ritonavir drug for antiretroviral-naïve patients is 400/100 mg twice a day or 800/200 mg once a day.

The recommended dosage of the combined lopinavir/ritonavir drug for non-naïve patients is 400/100 mg twice a day. Once-a-day administration for such patients is not recommended.

Effective dosage of an active substance of HIV protease inhibitor nelfinavir in dosage form is 750 mg.

Effective dosage of an active substance of HIV protease inhibitor darunavir in dosage form is 300 mg.

Effective dosage of an active substance of HIV protease inhibitor saquinavir in dosage form is 500 mg.

Effective dosage of an active substance of HIV protease inhibitor indinavir in dosage form is 400 mg.

Effective dosage of an active substance of HIV protease inhibitor tipranavir in dosage form is 500 mg.

Effective dosage of an active substance of HIV protease inhibitor fosamprenavir in dosage form is 1400 mg.

Also in accordance with the said invention, an HIV-infection treatment method is claimed, which includes administration to a mammal in need for such treatment the pharmaceutical composition in accordance with the said invention.

The administration method consists of administering a therapeutic dose of the solid dosage form of the pharmaceutical composition, which contains at least one HIV protease inhibitor in therapeutic amount, selected from the group of nelfinavir, saquinavir, tipranavir, darunavir, indinavir, ritonavir, lopinavir, palinavir, or fosamprenavir and pharmaceutically acceptable excipients; among the pharmaceutically acceptable excipients there should be at least one water-soluble polymer in the amount from 0.4 to 49% w/w of the total finished dosage form, at least one water-insoluble polymer in the amount from 0.39 to 28% w/w of the total finished dosage form, surfactants, fillers up to 100% w/w of the total finished dosage form.

In one of the variations, the administration method consists of administering a therapeutic dose of the solid dosage form of the pharmaceutical composition, which comprises of at least one HIV protease inhibitor in a therapeutic amount, selected from the group of nelfinavir, saquinavir, tipranavir, darunavir, indinavir, ritonavir, lopinavir, palinavir, or fosamprenavir and pharmaceutically acceptable excipients; among the pharmaceutically acceptable excipients there should be at least one water-insoluble polymer in the amount from 0.39 to 28% w/w of the total finished dosage form, surfactants, fillers up to 100% w/w of the total finished dosage form.

The following examples demonstrate (without limiting the scope of claim) the most preferable variations of embodiment of the invention; they also confirm the possibility of obtaining the claimed pharmaceutical composition and achievement of the stated technical results.

Example 1

Description of production technology for film-coated tablets:

Active pharmaceutical substances of the HIV protease inhibitor nelfinavir, saquinavir, tipranavir, darunavir, indinavir, ritonavir, lopinavir, palinavir, or fosamprenavir are separately micronised in the water-alcohol solution of surfactants polysorbate 80 and macrogol 6000 for 10 minutes with subsequent dissolution of the substances in D-Sorbitol and lactose carbohydrate and granulation. The blend is dried in a regular manner, in the fluid bed under the temperature of 60° C. until the moisture content of no more than 2.3% is achieved. It is then mixed and dusted by excipients in the following order until homogeneity is achieved: microcrystalline cellulose, sodium starch glycolate, croscarmellose sodium, copovidone (for example, Kollidon VA 64 Copovidone), low-substituted hydroxypropyl cellulose, colloidal silicon dioxide, sodium stearyl fumarate or magnesium stearate. From the obtained mass tablet-cores are formed and coated with water-soluble film.

Example 2

Description of production technology for film-coated lopinavir 100 mg+ritonavir 25 mg tablets Active pharmaceutical substances of lopinavir and ritonavir are separately micronised in water-alcohol (2:1) solution of sorbitol and polysorbate with macrogol for 10 minutes. Ritonavir suspension is blended with ¼ lactose and ¼ microcrystalline cellulose. The obtained granulate is dried in a flash drier under the temperature of 45° C. until moisture content of no more than 2.0% is achieved. Micronised lopinavir is homogenised with ¾ of lactose and microcrystalline cellulose, granulated, and flash dried under the temperature of 45° C. until moisture content of no more than 2.0-3.0% is achieved. The dried granulate is graded through a 30 mesh vibroscreen, mixed and dusted with low-substituted hydroxypropyl cellulose, colloidal silicon dioxide, and sodium stearyl fumarate in a conical mixer until homogeneous. Out of the powdered granulate 260 mg core-tablets are formed. The tablets are then coated with film in a coating apparatus through spraying of aqueous dispersion for film coating under the temperature of 50° C. until the tablet weight of 267 mg is achieved.

According to the Example 2 listed above, a pharmaceutical composition, which contained 28% w/w of water-insoluble polymers of the following composition, was obtained (all component ratios are provided in terms of 100% w/w of the total tablet weight), as seen in Table 1.

TABLE 1

A breakdown of components in a first composition of the present invention.

| | meas. units | tablet weight | % w/w |
|---|---|---|---|
| Core composition | | | |
| lopinavir substance | mg | 100 | 37.45 |
| ritonavir substance | mg | 25.0 | 9.36 |
| low-substituted hydroxypropylcellulose | mg | 16.02 | 6.00 |
| microcrystalline cellulose | mg | 58.74 | 22.00 |
| lactose | mg | 44.53 | 16.68 |
| sorbitol | mg | 9.61 | 3.60 |
| polysorbate 80 | mg | 1.30 | 0.49 |
| macrogol 6000 | mg | 1.30 | 0.49 |
| colloidal silicon dioxide | mg | 2.0 | 0.75 |
| sodium stearyl fumarate | mg | 1.50 | 0.56 |
| Total: tablet core | mg | 260 | 97.38 |
| Finished film: | | | |
| Adv. prima orange (hypromellose, talc, titanium dioxide, macrogol 6000, iron oxide red, yellow) | mg | 7 | 2.62 |
| Total: film-coated tablet | mg | 267 | 100 |

According to the Example 2 listed above, a pharmaceutical composition, which contained 0.39% w/w of water-insoluble polymers of the following composition, was obtained (all component ratios are provided in terms of 100% of the total tablet weight), seen in Table 2.

TABLE 2

A breakdown of components in a composition of the present invention.

| | meas. units | tablet weight | % w/w |
|---|---|---|---|
| Core composition | | | |
| lopinavir substance | mg | 100 | 37.45 |
| ritonavir substance | mg | 25.0 | 9.36 |
| low-sub stituted hydroxypropylcellulose | mg | 1.04 | 0.39 |
| lactose | mg | 112.08 | 41.98 |
| colloidal silicon dioxide | mg | 7.00 | 2.62 |
| sorbitol | mg | 9.61 | 3.60 |

TABLE 2-continued

A breakdown of components in a composition of the present invention.

|  | meas. units | tablet weight | % w/w |
|---|---|---|---|
| macrogol 6000 | mg | 1.30 | 0.49 |
| sodium stearyl fumarate | mg | 2.67 | 1.00 |
| polysorabte 80 | mg | 1.30 | 0.49 |
| Total: tablet core | mg | 260 | 97.38 |
| Finished film: | | | |
| Adv. prima orange (hypromellose, talc, titanium dioxide, macrogol 6000, iron oxide red, yellow) | mg | 7 | 2.62 |
| Total: film-coated tablet | mg | 267 | 100 |

Example 3

Oral Bioavailability Research Technique

Bioavailability research was conducted on male and female dogs weighing approximately 10 kg. During the course of the study all animals were fed a balanced diet containing 27% fat and given unlimited water. Every dog was given a 100 mcg/kg oral dose of histamine (approximately 30 minutes before study drug administration). Every dog was given oral doses containing 200 mg of lopinavir and 50 mg of ritonavir respectively (variation 1 and 2 of the claimed pharmaceutical composition). Afterwards, approximately 10 ml of water was given. Blood samples were collected from each animal before the dose and 0.25, 0.5, 1.0, 1.5, 2, 3, 4, 6, 8, 10, 12, and 24 hours after dose administration.

Plasma and red cells were separated centrifugally and frozen until analysis (−30° C.). HIV protease inhibitors were determined through reversed-phase high-performance liquid chromatography with shortwave UV-detection; following that, plasma samples were subjected to solvent extraction. During the study, the area under the curve (AUC) was calculated by using the trapezoidal rule method. Groups of 11-13 dogs were used for evaluation of each dosage form; the provided values are average for each group. Dose-dependent values of drug AUC in dogs by prototype were 10.22 mcg·h/ml/100 mg for ritonavir and 50.2 mcg·h/ml/100 mg for lopinavir. Dose-dependent values of drug AUC (variation 1 of the claimed pharmaceutical composition) in accordance with the said invention in dogs were 30.36 mcg·h/ml/100 mg for ritonavir and 66.2 mcg·h/ml/100 mg for lopinavir.

Dose-dependent values of drug AUC (variation 2 of pharmaceutical composition) in accordance with the said invention 28.36 mcg·h/ml/100 mg for ritonavir and 64.2 mcg·h/ml/100 mg for lopinavir.

The results of this study have shown that pharmaceutical composition bioavailability in accordance with the said invention was higher as compared to the prototype drug.

Example 4

Comparative study of dissolution kinetics of drugs "Kalidavir®, film-coated tablets (Lopinavir 100 mg+Ritonavir 25 mg)", manufactured at the JSC (Joint-Stock Company) Pharmasyntez, Russia, and "Kaletra, film-coated tablets (Lopinavir 200 mg+Ritonavir 50 mg)", manufactured at Abbott GmBH and Co.KG, Germany This study was conducted according to GPA (general pharmacopoeia article) 42-0003-04 "Dissolution" on a "paddle mixer" apparatus with rotation speed of 75 rpm under the temperature of 37±0.5° C. Dissolution medium— 1% sodium dodecyl sulfate solution. Dissolution medium volume—900 ml. Sampling time points: 15 min, 30 min, 60 min, 90 min, 120 min. Quantitative evaluation of the released lopinavir and ritonavir was conducted by HPLC (high-performance liquid chromatography).

Kalidavir and Kaletra dissolution profiles are provided in the Figure.

Average amount of lopinavir released within 15 min out of Kalidavir (manufactured at the JSC Pharmasyntez) was 47.09% (i.e., less than 85%), ritonavir—107.27% (more than 85%), out of Kaletra (manufactured at Abbott GmBH) the amount of released lopinavir was 27.03%, ritonavir—25.81% (i.e., less than 85%).

Thus, the obtained results show that the pharmaceutical composition in accordance with the said invention has better properties as compared to release profile of the prototype drug, which allows to increase bioavailability of the claimed pharmaceutical composition.

Example 5

According to the methodology, describe in Example 1, the produced pharmaceutical composition in a form of a film-coated tablet (lopinavir+ritonavir 200 mg+50 mg, 100 mg+25 mg) has the following components and ratios, % w/w (all component ratios are given in terms of 100% w/w of the total tablet weight), as seen in Table 3.

TABLE 3

A breakdown of components in a first composition of the present invention.

|  | meas. units | tablet weight | tablet weight | % w/w |
|---|---|---|---|---|
| Core composition | | | | |
| lopinavir substance | mg | 100 | 200 | 37.45 |
| ritonavir substance | mg | 25 | 50 | 9.36 |
| low-substituted hydroxy-propylcellulose | mg | 20 | 40 | 7.49 |
| macrogol 6000 | mg | 2.5 | 5 | 0.94 |
| lactose | mg | 70 | 140 | 26.22 |
| polysorbate 80 | mg | 2.5 | 5 | 0.94 |
| Copovidone (kollidon BA 64) | mg | 5.5 | 11 | 2.06 |
| sodium starch glycolate | mg | 15 | 30 | 5.62 |
| colloidal silicon dioxide | mg | 7 | 14 | 2.62 |
| croscarmellose sodium | mg | 10 | 20 | 3.74 |
| sodium stearyl fumarate | mg | 2.5 | 5 | 0.94 |
| Total: tablet core | mg | 260 | 520 | 100 |
| Finished film: | | | | |
| Adv. prima orange (hypromellose, talc, titanium dioxide, macrogol 6000, iron oxide red, yellow) | mg | 7 | 14 | 2.62 |
| Total: film-coated tablet | mg | 267 | 534 | 100 |

Example 6

The drug is formulated as 5 mg, 10 mg, 25 mg, 50 mg, 100 mg capsules, as seen in Table 4.

TABLE 4

A breakdown of components in a second composition of
the present invention, presented in various dosages.

| composition per capsule: | mg (%) | | | | |
|---|---|---|---|---|---|
| ritonavir | 10(5) | 25(12.5) | 50(25) | 100(50) | 121(60.5) |
| crospovidone | 10(5) | 10(5) | 10(5) | 10(5) | 10(5) |
| mannitol | 20(10) | 20(10) | 20(10) | 20(10) | 20(10) |
| lactose | 150(75) | 135(67.5) | 110(55) | 60(30) | 39(19.5) |
| macrogol 6000 | 8(4) | 8(4) | 8(4) | 8(4) | 8(4) |
| sodium stearyl fumarate | 2(1) | 2(1) | 2(1) | 2(1) | 2(1) |
| weight of capsule contents | 200(100) | 200(100) | 200(100) | 200(100) | 200(100) |
| water-soluble polymers (croscarmellose sodium) | 8(4) | 8(4) | 8(4) | 8(4) | 8(4) |
| water-insoluble polymers (crospovidone) | 10(5) | 10(5) | 10(5) | 10(5) | 10(5) |

The sieved powders of ritonavir in the amount of 50.0 g, crospovidone in the amount of 10.0 g, macrogol 6000 in the amount of 8.0 g are put into a tumble mill and micronised for 30 minutes. Micronised ritonavir blended together with macrogol 6000 and crospovidone is granulated in a fluid bed of 20% solution of lactose and mannitol. The produced granulated powder is dusted with 2.0 g of sodium stearyl fumarate in a conical mixer. Capsules are de-dusted and packed into polymer bottles or one-sided dose trays. 1000 drug capsules with a total content weight of 200.0 g or 0.200 g±10% are produced; every capsule contains 0.050 g±10% of the active ingredient.

Example 7

Film-coated lopinavir+ritonavir 100 mg+25 g tablets, seen in Table 5.

TABLE 5

A breakdown of components in a third
composition of the present invention.

| substance name | meas. unit | tablet weight | % w/w |
|---|---|---|---|
| lopinavir substance | mg | 100.000 | 37.4532 |
| ritonavirsubstance | mg | 25.000 | 9.3633 |
| Mannitol | mg | 4.000 | 1.4981 |
| Microcrystallinecellulose (MCC) | mg | 10.000 | 3.7453 |
| Lactose | mg | 90.600 | 33.9326 |
| polysorbate 80 | mg | 1.540 | 0.5768 |
| Copovidone | mg | 1.068 | 0.4000 |
| colloidal silicon dioxide | mg | 25.000 | 9.3633 |
| sodium stearyl fumarate | mg | 2.792 | 1.0457 |
| Total: tablet core | mg | 260.000 | 97.3783 |
| Total: finished film | mg | 7.0 | 2.6217 |
| Total: film-coated tablet | mg | 267.0 | 93.6330 |
| water-insoluble polymers: MCC | mg | 10.0 | 3.7453 |
| water-soluble polymers: copovidone | mg | 1.068 | 0.4000 |

Example 8

Comparative study of dissolution kinetics of drugs "Kalidavir®, film-coated tablets (Lopinavir 100 mg+Ritonavir 25 mg)", manufactured at the JSC Pharmasyntez, Russia, and a the prototype drug—"Kaletra, film-coated tablets (Lopinavir 200 mg+Ritonavir 50 mg)", manufactured at Abbott GmBH and Co.KG, Germany.

Series ZT 300 "Erweka" dissolution tester was used to determine the tablet dissolution time.

The dissolution time for tablets containing 0.39% w/w of water-insoluble polymers (qualitative and quantitative properties correspond to the properties, described in Example 1) was 15 min.

The dissolution time for tablets containing 28% w/w of water-insoluble polymers (qualitative and quantitative properties correspond to the [properties, described in Example 1) was 10 min.

Dissolution time of prototype tablets was 25 min.

Thus, the obtained results show that the pharmaceutical composition in accordance with the said invention has better dissolution properties as compared to the prototype Example 9

Study of influence of water-soluble and insoluble polymers content on bioavailability.

Non-inbred male rats weighing up to 300-350 g were selected for the oral bioavailability in-vivo study. Rats were kept in vivarium-like conditions with natural light regime and fed a standard laboratory animal diet (GOST P50258-92) in compliance with the International recommendation of the European Convention for the Protection of Vertebrate Animals used for Experimental and Other Scientific Purposes (1997), as well as good laboratory practices of preclinical studies in RF. Each rat was prepared by surgical permanent catheter implantation into superior vena cava. The rats were divided into 6 groups of 9. The I group was given an oral dose of the composition containing the following of water-soluble polymers in the amount of 0.4% w/w and water-insoluble polymers in the amount of 0.39% w/w, seen in Table 6.

TABLE 6

A breakdown of components in a fourth
composition of the present invention.

| Core composition: | mg | % w/w |
|---|---|---|
| lopinavir substance | 100 | 37.45 |
| ritonavir substance | 25 | 9.36 |
| low-substituted hydroxypropyl cellulose | 1.04 | 0.39 |
| copovidone | 1.068 | 0.40 |
| Lactose | 112.08 | 41.98 |
| colloidal silicon dioxide | 7 | 2.62 |
| Carbitol | 8.542 | 3.2 |
| macrogol 6000 | 1.3 | 0.49 |

TABLE 6-continued

A breakdown of components in a fourth
composition of the present invention.

| Core composition: | mg | % w/w |
|---|---|---|
| sodium stearyl fumarate | 2.67 | 1 |
| polysorbate 80(tween 80) | 1.3 | 0.49 |
| tablet core weight | 260 | 97.38 |
| finished film weight | 7 | 2.62 |
| film-coated tablet weight | 267 | 100 |

Water-insoluble polymers 0.39% w/w (1.04 mg), water-soluble polymers 0.4% w/w (1.068 mg).

The II group was given an oral dose of the composition containing the following of water-soluble polymers in the amount of 49% and water-insoluble polymers in the amount of 28% w/w, seen in Table 7.

TABLE 7

A breakdown of components in a fifth
composition of the present invention.

| | mg | % w/w |
|---|---|---|
| Core composition | | |
| Ritonavir substance | 6.55 | 5.00 |
| Low-substituted hydroxypropyl cellulose | 6.55 | 5.00 |
| Microcrystalline cellulose | 30.13 | 23.00 |
| Povidone | 64.19 | 49.00 |
| Sorbitol | 1.00 | 0.76 |
| Colloidal silicon dioxide | 2.00 | 1.53 |
| Lactose | 15.3 | 11.68 |
| Macrogol 6000 (polyethylene glycol) | 0.495 | 0.38 |
| Polysorbate 80 (tween 80) | 0.495 | 0.38 |
| Sodium stearyl fumarate | 0.79 | 0.60 |
| Total: tablet core weight | 127.5 | 97.33 |
| Finished film | | |
| Film weight | 3.5 | 2.67 |
| Film-coated tablet weight | 131 | 100 |

Water-soluble polymers (povidone)—49% w/w

Water-insoluble polymers (Low-substituted hydroxypropyl cellulose, microcrystallinecellulose)—28% w/w The III group of rats was given an oral dosage of the composition containing 0.39% w/w of water-insoluble polymers (pharmaceutical composition corresponds to the composition, described in Example 2).

The IV group of rats was given an oral dosage of the composition containing 28% w/w of the following water-insoluble polymers, seen in Table 8.

TABLE 8

A breakdown of components in a sixth
composition of the present invention.

| | mg | % w/w |
|---|---|---|
| Core composition | | |
| Lopinavir substance | 100 | 37.45 |
| Ritonavir substance | 25 | 9.36 |
| Low-substituted hydroxypropyl cellulose | 16.02 | 6.00 |
| Microcrystalline cellulose | 58.74 | 22.00 |
| Lactose | 44.53 | 16.68 |
| Sorbitol | 9.61 | 3.60 |
| Polysorbate 80 (tween 80) | 1.30 | 0.49 |
| Macrogol 6000 | 1.30 | 0.49 |
| Colloidal silicon dioxide | 2.00 | 0.75 |
| Sodium stearyl fumarate | 1.50 | 0.56 |
| Total: tablet core weight | 260 | 97.38 |
| Finished film | | |
| Film weight | 7.00 | 2.62 |
| Film-coated tablet weight | 267 | 100 |

Water-insoluble polymers (Low-substituted hydroxypropyl cellulose, microcrystalline cellulose)—28% w/w.

The IV group of rats was given an oral dosage of the composition containing 0.4% w/w of water-soluble polymers and 3.75% w/w of water-insoluble polymers. The pharmaceutical composition corresponds to the composition, describe in Example 7.

Kaletra® tablets were used as comparator, were given orally to group IV (control group) and had the following composition (g), as seen in Table 9.

TABLE 9

The composition of Kaletra tablets.
Active substances:

| Lopinavir | 100 mg, | ritonavir | 25 mg; |
|---|---|---|---|
| Excipients: | | | |

Copovidone K 28—426.9 mg; sorbitan laurate—41.95 mg; colloidal silicon dioxide—6.0 mg; second layer: sodium stearyl fumarate—6.15 mg; colloidal silicon dioxide—4.0 mg; film coating: Opadry® II pink 85 F 14399—15.0 mg, polyvinilalcohol—40.00%, titanium dioxide—24.85%, talc—14.80%, macrogol 3350—20.20%, iron oxide red E172—0.15%.

Comparator drugs were given once in a dose that nominally corresponds to the ⅕ of a dose recommended for humans.

Consecutive blood samples of 0.25 ml were collected via the permanent catheter in 0.25, 0.5, 1, 2, 4, 6, 8, 12, and 24 hours after drug administration. These samples were analysed using an HPLC assay for the tested compounds. Each of the three composition concentrations were plotted against the time after oral administration, and AUC (area under the curve of plasma concentration vs. time) was integrated using trapezoidal method for calculation of absolute bioavailability, reflected in Table 10.

TABLE 10

The bioavailability of the test compositions
in the model study groups.

| Rat study group | Mean absolute oral bioavailability(%) |
|---|---|
| I | 86 |
| II | 96 |
| III | 79 |
| IV | 85 |
| V | 88 |
| VI(control group) | 75 |

Thus, the results of the conducted studies have unexpectedly shown that the pharmaceutical composition containing 0.4% w/w of water-soluble polymers and 0.39% w/w of water-insoluble polymers allowed for an 11% increase of absolute bioavailability as compared to the prototype. Pharmaceutical composition containing 49% w/w of water-soluble polymers and 28% w/w of water-insoluble polymers allowed for a 21% increase of absolute availability as compared to the prototype. For the pharmaceutical composition containing 0.39% w/w of water-insoluble polymers, the absolute bioavailability was similar to the prototype composition, but was 4% higher. For the pharmaceutical composition containing 28% w/w of water-insoluble polymers, the absolute bioavailability was 10% higher and had a value of 85%.

The authors of the said invention have unexpectedly discovered that the content of water-soluble and insoluble polymers within the claimed compositions has an effect on such technological properties as strength and ductility of the dosage form. The results of the conducted studies have shown that the finished dosage forms (tablets) containing water-soluble polymers in the amount between 0.4 and 49% w/w, as well as water-insoluble polymers in the amount between 0.3 and 28% w/w are stronger compared to the prototype. Additionally, tablets in accordance with the said invention also have higher ductility due to the use of high-ductile polymers, which leads to smaller losses during tabletisation, increases tabletisation speed, and provides for easier swallowing of the tablets.

Mechanical strength of the tablets was measured by tablet friability. The evaluation of tablet friability was conducted on an Agilent Friability Tester. Prototype tablet strength by friability was 98%. Strength of tablets containing 0.4% of water-soluble polymers and 0.39% of water-insoluble polymers was 99.4%. Strength of tablets containing 49% of water-soluble polymers and 28% of water-insoluble polymers was 99.8%. Strength of tablets containing 0.39% of water-insoluble polymers was 99%. Strength of tablets containing 28% of water-insoluble polymers was 99.2%.

Thus, the claimed invention allows to obtain new and more effective (compared to the prototype) pharmaceutical composition with improved technological properties (strength, ductility, disintegration ability), as well as improved dissolution kinetics and increased (compared to the prototype) bioavailability.

What is claimed is:

1. A pharmaceutical composition comprising:
   at least one HIV protease inhibitor in a therapeutic amount, selected from the group consisting of ritonavir, and lopinavir;
   a plurality of pharmaceutically acceptable excipients, comprising:
      at least one water-soluble polymer in an amount of 0.4-20% w/w of a total dosage form;
      wherein the at least one water-soluble polymer is water-soluble at 20° C.;
      at least one water-insoluble polymer in an amount of 0.39-28% w/w of the total dosage form;
      wherein the at least one water-insoluble polymer is water-insoluble at 20° C.;
      at least two surfactants, wherein the at least two surfactants includes at least one of polysorbate 80 and macrogol 6000; and
      at least two fillers, wherein when the fillers comprise water-soluble and/or water-insoluble polymers the amount of the at least one water-soluble polymer and the amount of the at least one water-insoluble polymer include the fillers correspondingly;
   wherein the plurality of pharmaceutically acceptable excipients and the at least one HIV protease inhibitor comprise up to 100% w/w of the total dosage form;
   wherein the at least one HIV protease inhibitor and the at least one water-insoluble polymer are in a ratio of between 2.5:1 to 120:1; and
   wherein lower concentrations of the water-soluble polymers by weight increases bioavailability in comparison to similar compositions with higher concentrations by weight of the water-soluble polymers.

2. The pharmaceutical composition according to claim 1, wherein the at least one water-soluble polymer is copovidone.

3. The pharmaceutical composition according to claim 1, wherein the at least one water-soluble polymer is sodium starch glycolate.

4. The pharmaceutical composition according to claim 1, wherein the at least one water-soluble polymer is croscarmellose sodium, homopolymers and copolymers of N-vinyl lactams, polyethylene oxide, polypropylene oxide, copolymers of ethylene oxide and propylene oxide, polyacrylates, polymethacrylates, polyacrylamides, vinyl acetate polymers, polyvinyl alcohol, carrageenans, cellulose esters, cellulose ethers, cellulose succinates, or combinations thereof.

5. The pharmaceutical composition according to claim 1, wherein the at least one water-insoluble polymer is microcrystalline cellulose.

6. The pharmaceutical composition according to claim 1, wherein the at least one water-insoluble polymer is low-substituted hydroxypropyl cellulose.

7. The pharmaceutical composition according to claim 1, wherein the at least two surfactants are in an amount between 0.3-1.0% w/w.

8. The pharmaceutical composition according to claim 1, wherein the at least two fillers are in an amount between 0.3-56% w/w.

9. The pharmaceutical composition according to claim 8, wherein the at least two fillers comprise lactose, modified lactose, sucrose, glucose, mannitol, modified mannitol, sorbitol, fructose, cellulose, cellulose derivatives, starch, modified starch, dextrin, dextrose, dextrate, maltodextrine, calcium, calcium phosphate salt, calcium carbonate salt, calcium chloride salt, magnesium, magnesium oxide, magnesium carbonate, magnesium stearate, crospovidone, cyclodextrines, alginic acid, alginic acid salt, saccharine, saccharine salt, sodium chloride salt, sodium citrate salt, sodium fumarate salt, sodium carbonate salt, aspartame, lactic acid, lactic acid salt, succinic acid, ascorbic acid, tartaric acid, colloidal silicon dioxide, cyclamate, benzoic acid, benzoic acid salts, parabens, parabens salts, or combinations thereof.

10. A pharmaceutical composition comprising:
   at least one HIV protease inhibitor in a therapeutic amount, selected from the group consisting of ritonavir, and lopinavir;
   a plurality of pharmaceutically acceptable excipients, comprising:
      at least one water-insoluble polymer in an amount of 0.39-28% w/w of a total dosage form;
      wherein the at least one water-insoluble polymer is water-insoluble at 20° C.;
      at least two surfactants, wherein the at least two surfactants includes at least one of polysorbate 80 and macrogol 6000; and at least two fillers, wherein when the fillers comprise water-soluble and/or water-insoluble polymers the amount of the at least one water-soluble polymer and the amount of the at least one water-insoluble polymer include the fillers correspondingly;

wherein the plurality of pharmaceutically acceptable excipients and the at least one HIV protease inhibitor comprise up to 100% w/w of the total dosage form, wherein water-soluble polymers are absent from the composition;

wherein the water-soluble polymers are water-soluble at 20° C.;

wherein the at least one HIV protease inhibitor and the at least one water-insoluble polymer are in a ratio of between 2.5:1 to 120:1; and wherein absence of the water-soluble polymers increases bioavailability in comparison to compositions with higher concentrations by weight of the water-soluble polymers.

11. The pharmaceutical composition according to claim 10, wherein the at least one water-insoluble polymer is microcrystalline cellulose.

12. The pharmaceutical composition according to claim 10, wherein the at least one water-insoluble polymer is low-substituted hydroxypropyl cellulose.

13. The pharmaceutical composition according to claim 10, wherein the at least two surfactants are in an amount between 0.3-1.0% w/w.

14. The pharmaceutical composition according to claim 10, wherein the at least two fillers are in an amount between 0.3-56% w/w.

15. The pharmaceutical composition according to claim 10, wherein the at least two fillers comprise lactose, modified lactose, sucrose, glucose, mannitol, modified mannitol, sorbitol, fructose, cellulose, cellulose derivatives, starch, modified starch, dextrin, dextrose, dextrate, maltodextrine, calcium, calcium phosphate salt, calcium carbonate salt, calcium chloride salt, magnesium, magnesium oxide, magnesium carbonate, magnesium stearate, crospovidone, cyclodextrines, alginic acid, alginic acid salt, saccharine, saccharine salt, sodium chloride salt, sodium citrate salt, sodium fumarate salt, sodium carbonate salt, aspartame, lactic acid, lactic acid salt, succinic acid, ascorbic acid, tartaric acid, colloidal silicon dioxide, cyclamate, benzoic acid, benzoic acid salts, parabens, parabens salts, or combinations thereof.

16. A pharmaceutical composition comprising:
at least one HIV protease inhibitor in a therapeutic amount, selected from the group consisting of ritonavir, and lopinavir;
a plurality of pharmaceutically acceptable excipients, comprising:
at least one water-soluble polymer in an amount of 0.4-20% w/w of a total dosage form;
wherein the at least one water-soluble polymer is water-soluble at 20° C.;
at least one water-insoluble polymer in an amount of 0.39-28% w/w of the total dosage form;
wherein the at least one water-insoluble polymer is water-insoluble at 20° C.;
at least two surfactants, wherein the at least two surfactants includes at least one of polysorbate 80 and macrogol 6000; and
at least two fillers, wherein the fillers are selected from the group consisting of lactose, sucrose, glucose, mannitol, sorbitol, fructose, cellulose, cellulose derivatives, starch, dextrin, dextrose, dextrate, maltodextrine, calcium and its salts (phosphates, carbonates, chlorides), magnesium and its derivatives (oxide, carbonate, stearate), cyclodextrines, alginic acid and its salts, saccharine and its salts, sodium salts (chloride, citrate, fumarate, carbonate), aspartame, lactic acid ant its salts, succinic acid, ascorbic acid, tartaric acid, colloidal silicon dioxide, cyclamate, benzoic acid and its salts, and parabens and its salts;
wherein the plurality of pharmaceutically acceptable excipients and the at least one HIV protease inhibitor comprise up to 100% w/w of the total dosage form;
wherein the at least one HIV protease inhibitor and the at least one water-insoluble polymer are in a ratio of between 2.5:1 to 120:1; and
wherein lower concentrations of the water-soluble polymers by weight increases bioavailability in comparison to similar compositions with higher concentrations by weight of the water-soluble polymers.

17. A pharmaceutical composition comprising:
at least one HIV protease inhibitor in a therapeutic amount, selected from the group consisting of ritonavir, and lopinavir;
a plurality of pharmaceutically acceptable excipients, comprising:
at least one water-insoluble polymer in an amount of 0.39-28% w/w of a total dosage form;
wherein the at least one water-insoluble polymer is water-insoluble at 20° C.;
at least two surfactants, wherein the at least two surfactants includes at least one of polysorbate 80 and macrogol 6000; and
at least two fillers, wherein the fillers are selected from the group consisting of lactose, sucrose, glucose, mannitol, sorbitol, fructose, cellulose, cellulose derivatives, starch, dextrin, dextrose, dextrate, maltodextrine, calcium and its salts (phosphates, carbonates, chlorides), magnesium and its derivatives (oxide, carbonate, stearate), cyclodextrines, alginic acid and its salts, saccharine and its salts, sodium salts (chloride, citrate, fumarate, carbonate), aspartame, lactic acid ant its salts, succinic acid, ascorbic acid, tartaric acid, colloidal silicon dioxide, cyclamate, benzoic acid and its salts, and parabens and its salts;
wherein the plurality of pharmaceutically acceptable excipients and the at least one HIV protease inhibitor comprise up to 100% w/w of the total dosage form,
wherein water-soluble polymers are absent from the composition;
wherein the water-soluble polymers are water-soluble at 20° C.;
wherein the at least one HIV protease inhibitor and the at least one water-insoluble polymer are in a ratio of between 2.5:1 to 120:1; and
wherein absence of the water-soluble polymers increases bioavailability in comparison to compositions with higher concentrations by weight of the water-soluble polymers.

* * * * *